US012642938B2

(12) United States Patent
Howell

(10) Patent No.: US 12,642,938 B2
(45) Date of Patent: Jun. 2, 2026

(54) RAPIDLY INSERTABLE CENTRAL CATHETERS AND METHODS THEREOF

(71) Applicant: Bard Access Systems, Inc., Salt Lake City, UT (US)

(72) Inventor: Glade H. Howell, Draper, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 1015 days.

(21) Appl. No.: 17/363,500

(22) Filed: Jun. 30, 2021

(65) Prior Publication Data

US 2022/0001138 A1     Jan. 6, 2022

Related U.S. Application Data

(60) Provisional application No. 63/047,118, filed on Jul. 1, 2020.

(51) Int. Cl.
A61M 25/00 (2006.01)
A61M 25/06 (2006.01)

(52) U.S. Cl.
CPC .... A61M 25/0029 (2013.01); A61M 25/0009 (2013.01); A61M 25/06 (2013.01)

(58) Field of Classification Search
CPC .......... A61M 25/0029; A61M 25/0009; A61M 25/06; A61M 25/0012; A61M 25/0014;
(Continued)

(56) References Cited

U.S. PATENT DOCUMENTS

| | | | |
|---|---|---|---|
| 1,013,691 A | 1/1912 | Shields | |
| 1,906,678 A | 5/1933 | Wappler | |

(Continued)

FOREIGN PATENT DOCUMENTS

| | | |
|---|---|---|
| EP | 0730880 A1 | 9/1996 |
| EP | 2061385 A1 | 5/2009 |

(Continued)

OTHER PUBLICATIONS

PCT/US2021/039084 filed Jun. 25, 2021 International Search Report and Written Opinion dated Jan. 10, 2022.
(Continued)

*Primary Examiner* — James D Ponton
*Assistant Examiner* — John A Doubrava
(74) *Attorney, Agent, or Firm* — Rutan & Tucker LLP

(57) ABSTRACT

Rapidly insertable central catheters ("RICCs") and methods are disclosed. A RICC can include a first section of a first polymeric material in a distal portion of a catheter tube, a second section of a second polymeric material proximal of the first section, and a tapered junction therebetween. The first polymeric material has a first durometer. The second polymeric material has a second, lesser durometer. The junction is formed of the second polymeric material or a third polymeric material having a third durometer closer to the second durometer than the first durometer. The first section has a proximal portion disposed in a receptacle of the junction. An abluminal surface of a distal portion of the junction smoothly transitions onto an abluminal surface of the proximal portion of the first section without an edge that catches on skin when the RICC is inserted into an insertion site of a patient.

10 Claims, 9 Drawing Sheets

(58) Field of Classification Search
CPC .......... A61M 25/0026; A61M 25/0043; A61M
25/0102; A61M 25/0113; A61M 25/0606;
A61M 25/065; A61M 25/09041; A61M
2025/0183; A61M 2210/12
See application file for complete search history.

(56) References Cited

U.S. PATENT DOCUMENTS

| | | |
|---|---|---|
| 3,225,762 A | 12/1965 | Guttman |
| 3,710,781 A | 1/1973 | Huthcins, IV et al. |
| 3,890,976 A | 6/1975 | Bazell et al. |
| 4,205,675 A | 6/1980 | Vaillancourt |
| 4,270,535 A | 6/1981 | Bogue et al. |
| 4,292,970 A | 10/1981 | Hession, Jr. |
| 4,468,224 A | 8/1984 | Enzmann et al. |
| 4,525,157 A | 6/1985 | Vaillancourt |
| 4,581,019 A | 4/1986 | Curelaru et al. |
| 4,661,300 A | 4/1987 | Daugherty |
| 5,004,455 A | 4/1991 | Greenwood et al. |
| 5,017,259 A | 5/1991 | Kohsai |
| 5,040,548 A | 8/1991 | Yock |
| 5,057,073 A | 10/1991 | Martin |
| 5,112,312 A | 5/1992 | Luther |
| 5,120,317 A | 6/1992 | Luther |
| 5,135,599 A | 8/1992 | Martin et al. |
| 5,167,623 A | 12/1992 | Cianci et al. |
| 5,188,593 A | 2/1993 | Martin |
| 5,195,962 A | 3/1993 | Martin et al. |
| 5,207,650 A | 5/1993 | Martin |
| 5,267,958 A | 12/1993 | Buchbinder et al. |
| 5,295,970 A | 3/1994 | Clinton et al. |
| 5,306,247 A | 4/1994 | Pfenninger |
| 5,328,472 A | 7/1994 | Steinke et al. |
| 5,350,358 A | 9/1994 | Martin |
| 5,368,567 A | 11/1994 | Lee |
| 5,378,230 A | 1/1995 | Mahurkar |
| 5,380,290 A | 1/1995 | Makower et al. |
| 5,389,087 A | 2/1995 | Miraki |
| 5,439,449 A | 8/1995 | Mapes et al. |
| 5,443,457 A | 8/1995 | Ginn et al. |
| 5,489,271 A | 2/1996 | Andersen |
| 5,573,520 A | 11/1996 | Schwartz et al. |
| 5,645,528 A | 7/1997 | Thome |
| 5,683,370 A | 11/1997 | Luther et al. |
| 5,690,613 A | 11/1997 | Verbeek |
| 5,718,678 A | 2/1998 | Fleming, III |
| 5,772,636 A | 6/1998 | Brimhall et al. |
| 5,810,789 A | 9/1998 | Powers et al. |
| 5,885,251 A | 3/1999 | Luther |
| 5,908,409 A | 6/1999 | Rinehart et al. |
| 5,919,164 A | 7/1999 | Andersen |
| 5,947,940 A | 9/1999 | Beisel |
| 5,957,893 A | 9/1999 | Luther et al. |
| 6,206,849 B1 | 3/2001 | Martin et al. |
| 6,332,877 B1 | 12/2001 | Michels |
| 6,475,187 B1 | 11/2002 | Gerberding |
| 6,606,515 B1 | 8/2003 | Windheuser et al. |
| 6,716,228 B2 | 4/2004 | Tal |
| 6,726,659 B1 | 4/2004 | Stocking et al. |
| 6,819,951 B2 | 11/2004 | Patel et al. |
| 6,821,287 B1 | 11/2004 | Jang |
| 6,926,692 B2 | 8/2005 | Katoh et al. |
| 6,962,575 B2 | 11/2005 | Tal |
| 6,994,693 B2 | 2/2006 | Tal |
| 6,999,809 B2 | 2/2006 | Currier et al. |
| 7,025,746 B2 | 4/2006 | Tal |
| 7,029,467 B2 | 4/2006 | Currier et al. |
| 7,037,293 B2 | 5/2006 | Carrillo et al. |
| 7,074,231 B2 | 7/2006 | Jang |
| 7,141,050 B2 | 11/2006 | Deal et al. |
| 7,144,386 B2 | 12/2006 | Korkor et al. |
| 7,311,697 B2 | 12/2007 | Osborne |
| 7,364,566 B2 | 4/2008 | Elkins et al. |
| 7,377,910 B2 | 5/2008 | Katoh et al. |
| 7,390,323 B2 | 6/2008 | Jang |
| D600,793 S | 9/2009 | Bierman et al. |
| D601,242 S | 9/2009 | Bierman et al. |
| D601,243 S | 9/2009 | Bierman et al. |
| 7,594,911 B2 | 9/2009 | Powers et al. |
| 7,691,093 B2 | 4/2010 | Brimhall |
| 7,722,567 B2 | 5/2010 | Tal |
| D617,893 S | 6/2010 | Bierman et al. |
| D624,643 S | 9/2010 | Bierman et al. |
| 7,819,889 B2 | 10/2010 | Healy et al. |
| 7,857,788 B2 | 12/2010 | Racz |
| D630,729 S | 1/2011 | Bierman et al. |
| 7,909,797 B2 | 3/2011 | Kennedy, II et al. |
| 7,909,811 B2 | 3/2011 | Agro et al. |
| 7,922,696 B2 | 4/2011 | Tal et al. |
| 7,938,820 B2 | 5/2011 | Webster et al. |
| 7,967,834 B2 | 6/2011 | Tal et al. |
| 7,985,204 B2 | 7/2011 | Katoh et al. |
| 8,073,517 B1 | 12/2011 | Burchman |
| 8,105,286 B2 | 1/2012 | Anderson et al. |
| 8,192,402 B2 | 6/2012 | Anderson et al. |
| 8,202,251 B2 | 6/2012 | Bierman et al. |
| 8,206,356 B2 | 6/2012 | Katoh et al. |
| 8,372,107 B2 | 2/2013 | Tupper |
| 8,377,006 B2 | 2/2013 | Tal et al. |
| 8,454,577 B2 | 6/2013 | Joergensen et al. |
| 8,585,858 B2 | 11/2013 | Kronfeld et al. |
| 8,657,790 B2 | 2/2014 | Tal et al. |
| 8,672,888 B2 | 3/2014 | Tal |
| 8,696,645 B2 | 4/2014 | Tal et al. |
| 8,784,362 B2 | 7/2014 | Boutilette et al. |
| 8,827,958 B2 | 9/2014 | Bierman et al. |
| 8,876,704 B2 | 11/2014 | Golden et al. |
| 8,882,713 B1 | 11/2014 | Call et al. |
| 8,900,192 B2 | 12/2014 | Anderson et al. |
| 8,900,207 B2 | 12/2014 | Uretsky |
| 8,915,884 B2 | 12/2014 | Tal et al. |
| 8,956,327 B2 | 2/2015 | Bierman et al. |
| 9,023,093 B2 | 5/2015 | Pal |
| 9,138,252 B2 | 9/2015 | Bierman et al. |
| 9,180,275 B2 | 11/2015 | Helm |
| 9,265,920 B2 | 2/2016 | Rundquist et al. |
| 9,272,121 B2 | 3/2016 | Piccagli |
| 9,522,254 B2 | 12/2016 | Belson |
| 9,554,785 B2 | 1/2017 | Walters et al. |
| 9,566,087 B2 | 2/2017 | Bierman et al. |
| 9,675,784 B2 | 6/2017 | Belson |
| 9,713,695 B2 | 7/2017 | Bunch et al. |
| 9,764,117 B2 | 9/2017 | Bierman et al. |
| 9,770,573 B2 | 9/2017 | Golden et al. |
| 9,814,861 B2 | 11/2017 | Boutillette et al. |
| 9,820,845 B2 | 11/2017 | von Lehe et al. |
| 9,861,383 B2 | 1/2018 | Clark |
| 9,884,169 B2 | 2/2018 | Bierman et al. |
| 9,889,275 B2 | 2/2018 | Voss et al. |
| 9,913,585 B2 | 3/2018 | McCaffrey et al. |
| 9,913,962 B2 | 3/2018 | Tal et al. |
| 9,950,139 B2 | 4/2018 | Blanchard et al. |
| 9,981,113 B2 | 5/2018 | Bierman |
| 10,010,312 B2 | 7/2018 | Tegels |
| 10,065,020 B2 | 9/2018 | Gaur |
| 10,098,724 B2 | 10/2018 | Adams et al. |
| 10,111,683 B2 | 10/2018 | Tsamir et al. |
| 10,118,020 B2 | 11/2018 | Avneri et al. |
| 10,130,269 B2 | 11/2018 | McCaffrey et al. |
| 10,220,184 B2 | 3/2019 | Clark |
| 10,220,191 B2 | 3/2019 | Belson et al. |
| 10,265,508 B2 | 4/2019 | Baid |
| 10,271,873 B2 | 4/2019 | Steingisser et al. |
| 10,376,675 B2 | 8/2019 | Mitchell et al. |
| 10,675,440 B2 | 6/2020 | Abitabilo et al. |
| 10,806,901 B2 | 10/2020 | Burkholz et al. |
| 2001/0044594 A1 | 11/2001 | Martin et al. |
| 2002/0040231 A1 | 4/2002 | Wysoki |
| 2002/0107506 A1 | 8/2002 | McGuckin et al. |
| 2002/0198492 A1 | 12/2002 | Miller et al. |
| 2003/0036712 A1 | 2/2003 | Heh et al. |
| 2003/0060863 A1 | 3/2003 | Dobak |
| 2003/0088212 A1 | 5/2003 | Tal |
| 2003/0100849 A1 | 5/2003 | Jang |

(56) References Cited

U.S. PATENT DOCUMENTS

2003/0153874 A1 8/2003 Tal
2003/0158514 A1 8/2003 Tal
2004/0116901 A1 6/2004 Appling
2004/0193093 A1 9/2004 Desmond
2004/0230178 A1 11/2004 Wu
2005/0004554 A1 1/2005 Osborne
2005/0049552 A1 3/2005 Holzapfel et al.
2005/0245882 A1 11/2005 Elkins et al.
2005/0283221 A1 12/2005 Mann et al.
2006/0009740 A1* 1/2006 Higgins .............. A61M 25/001
                                                          604/525
2006/0116629 A1 6/2006 Tal et al.
2006/0129100 A1 6/2006 Tal
2006/0129130 A1 6/2006 Tal et al.
2008/0039796 A1 2/2008 Nakajima
2008/0045894 A1 2/2008 Perchik et al.
2008/0125744 A1 5/2008 Treacy
2008/0125748 A1 5/2008 Patel
2008/0262430 A1 10/2008 Anderson et al.
2008/0262431 A1 10/2008 Anderson et al.
2008/0294111 A1 11/2008 Tal et al.
2008/0312578 A1 12/2008 DeFonzo et al.
2009/0093670 A1 4/2009 Annest et al.
2009/0221961 A1 9/2009 Tal et al.
2009/0270889 A1 10/2009 Tal et al.
2010/0256487 A1 10/2010 Hawkins et al.
2010/0305474 A1 12/2010 DeMars et al.
2011/0004162 A1 1/2011 Tal
2011/0009827 A1 1/2011 Bierman et al.
2011/0021994 A1 1/2011 Anderson et al.
2011/0066142 A1 3/2011 Tal et al.
2011/0144620 A1 6/2011 Tal
2011/0152836 A1 6/2011 Riopelle et al.
2011/0202006 A1 8/2011 Bierman et al.
2011/0251559 A1 10/2011 Tal et al.
2011/0270192 A1 11/2011 Anderson et al.
2012/0041371 A1 2/2012 Tal et al.
2012/0065590 A1 3/2012 Bierman et al.
2012/0078231 A1 3/2012 Hoshinouchi
2012/0130411 A1 5/2012 Tal et al.
2012/0130415 A1 5/2012 Tal et al.
2012/0157854 A1 6/2012 Kurrus et al.
2012/0209221 A1 8/2012 Patterson et al.
2012/0220942 A1 8/2012 Hall et al.
2012/0283640 A1 11/2012 Anderson et al.
2012/0316500 A1 12/2012 Bierman et al.
2013/0012924 A1 1/2013 Davis et al.
2013/0053826 A1 2/2013 Shevgoor
2013/0123704 A1 5/2013 Bierman et al.
2013/0158338 A1 6/2013 Kelly et al.
2013/0188291 A1 7/2013 Vardiman
2013/0237931 A1 9/2013 Tal et al.
2013/0306079 A1 11/2013 Tracy
2014/0025036 A1 1/2014 Bierman et al.
2014/0081210 A1 3/2014 Bierman et al.
2014/0094741 A1 4/2014 Bellisario et al.
2014/0100552 A1 4/2014 Gallacher et al.
2014/0155863 A1* 6/2014 Walker .................. A61M 25/00
                                                          604/113
2014/0180255 A1* 6/2014 LeBlanc ............. A61M 25/008
                                                          604/524
2014/0207052 A1 7/2014 Tal et al.
2014/0207069 A1 7/2014 Bierman et al.
2014/0214005 A1 7/2014 Belson
2014/0257111 A1 9/2014 Yamashita et al.
2014/0276432 A1 9/2014 Bierman et al.
2014/0276599 A1 9/2014 Cully et al.
2015/0080939 A1 3/2015 Adams et al.
2015/0112310 A1 4/2015 Call et al.
2015/0126930 A1 5/2015 Bierman et al.
2015/0148595 A1 5/2015 Bagwell et al.
2015/0190168 A1 7/2015 Bierman et al.
2015/0196210 A1 7/2015 McCaffrey et al.
2015/0224287 A1 8/2015 Bian et al.
2015/0283357 A1 10/2015 Lampropoulos et al.

2015/0297868 A1 10/2015 Tal et al.
2015/0320969 A1 11/2015 Haslinger et al.
2015/0351793 A1 12/2015 Bierman et al.
2015/0359549 A1 12/2015 Lenker et al.
2015/0359998 A1 12/2015 Carmel et al.
2016/0082223 A1 3/2016 Barnell
2016/0114124 A1 4/2016 Tal
2016/0220786 A1* 8/2016 Mitchell ........... A61M 25/0029
2016/0220795 A1 8/2016 Korkuch et al.
2016/0325073 A1 11/2016 Davies et al.
2016/0338728 A1 11/2016 Tal
2016/0346503 A1 12/2016 Jackson et al.
2017/0035989 A1 2/2017 Gilman
2017/0035990 A1 2/2017 Swift
2017/0072165 A1 3/2017 Lim et al.
2017/0120000 A1 5/2017 Osypka et al.
2017/0128700 A1 5/2017 Roche Rebollo
2017/0172653 A1 6/2017 Urbanski et al.
2017/0239443 A1 8/2017 Abitabilo et al.
2017/0273713 A1 9/2017 Shah et al.
2017/0296792 A1 10/2017 Ornelas Vargas et al.
2017/0326339 A1 11/2017 Bailey et al.
2017/0333681 A1 11/2017 Di Caprio et al.
2017/0361070 A1 12/2017 Hivert
2018/0021545 A1 1/2018 Mitchell et al.
2018/0116690 A1 5/2018 Sarabia et al.
2018/0117284 A1 5/2018 Appling et al.
2018/0133438 A1 5/2018 Hulvershorn et al.
2018/0154062 A1 6/2018 DeFonzo et al.
2018/0154112 A1 6/2018 Chan et al.
2018/0193042 A1 7/2018 Wilson et al.
2018/0296799 A1 10/2018 Horst et al.
2018/0296804 A1 10/2018 Bierman
2018/0339131 A1 11/2018 Muse et al.
2019/0015646 A1 1/2019 Matlock et al.
2019/0060616 A1 2/2019 Solomon
2019/0076167 A1 3/2019 Fantuzzi et al.
2019/0134349 A1 5/2019 Cohn et al.
2019/0255294 A1 8/2019 Mitchell et al.
2019/0276268 A1 9/2019 Akingba
2019/0321590 A1 10/2019 Burkholz et al.
2020/0016374 A1 1/2020 Burkholz et al.
2020/0030124 A1 1/2020 Bluecher et al.
2020/0094025 A1 3/2020 Wisman
2021/0069471 A1 3/2021 Howell
2021/0121661 A1 4/2021 Howell
2021/0121667 A1 4/2021 Howell
2021/0187245 A1 6/2021 Ishida
2021/0322729 A1 10/2021 Howell
2021/0330941 A1 10/2021 Howell et al.
2021/0330942 A1 10/2021 Howell
2021/0361915 A1 11/2021 Howell et al.
2021/0402149 A1 12/2021 Howell
2021/0402153 A1 12/2021 Howell et al.
2022/0032013 A1 2/2022 Howell et al.
2022/0040447 A1 2/2022 Mewissen
2023/0126869 A1 4/2023 Sepulveda et al.
2023/0132903 A1 5/2023 Sepulveda et al.
2023/0233796 A1 7/2023 Howell
2023/0233800 A1 7/2023 Howell et al.
2024/0091501 A1 3/2024 Howell
2024/0181210 A1 6/2024 Howell et al.
2024/0198042 A1 6/2024 Sepulveda

FOREIGN PATENT DOCUMENTS

EP 1458437 B1 3/2010
EP 2248549 A2 11/2010
EP 2319576 A1 5/2011
EP 2366422 A1 9/2011
EP 2486880 A2 8/2012
EP 2486881 A2 8/2012
EP 2486951 A2 8/2012
EP 2512576 A2 10/2012
EP 2152348 B1 2/2015
EP 3093038 B1 5/2019
EP 2260897 B1 9/2019
ES 2303546 T3 8/2008
GB 1273547 A 5/1972

(56) References Cited

FOREIGN PATENT DOCUMENTS

| | | | |
|---|---|---|---|
| WO | 94/21315 | A1 | 9/1994 |
| WO | 95/32009 | A2 | 11/1995 |
| WO | 98/44979 | A1 | 10/1998 |
| WO | 98/53871 | A1 | 12/1998 |
| WO | 99/12600 | A1 | 3/1999 |
| WO | 99/26681 | A1 | 6/1999 |
| WO | 2003008020 | A1 | 1/2003 |
| WO | 2003057272 | A2 | 7/2003 |
| WO | 2003066125 | A2 | 8/2003 |
| WO | 2004037331 | A1 | 5/2004 |
| WO | 2006055288 | A2 | 5/2006 |
| WO | 2006055780 | A2 | 5/2006 |
| WO | 2007046850 | A2 | 4/2007 |
| WO | 2008033983 | A1 | 3/2008 |
| WO | 2008092029 | A2 | 7/2008 |
| WO | 2008/131300 | A2 | 10/2008 |
| WO | 2008131289 | A2 | 10/2008 |
| WO | 2009114833 | A1 | 9/2009 |
| WO | 2009114837 | A2 | 9/2009 |
| WO | 2010/048449 | A2 | 4/2010 |
| WO | 2010056906 | A2 | 5/2010 |
| WO | 2010083467 | A2 | 7/2010 |
| WO | 2010/132608 | A2 | 11/2010 |
| WO | 2011081859 | A2 | 7/2011 |
| WO | 2011097639 | A2 | 8/2011 |
| WO | 2011146764 | A1 | 11/2011 |
| WO | 2012068162 | A2 | 5/2012 |
| WO | 2012068166 | A2 | 5/2012 |
| WO | 2012135761 | A1 | 10/2012 |
| WO | 2012162677 | A1 | 11/2012 |
| WO | 2013026045 | A1 | 2/2013 |
| WO | 2013138519 | A1 | 9/2013 |
| WO | 2014006403 | A1 | 1/2014 |
| WO | 2014/100392 | A1 | 6/2014 |
| WO | 2014113257 | A2 | 7/2014 |
| WO | 2014152005 | A2 | 9/2014 |
| WO | 2014197614 | A2 | 12/2014 |
| WO | 2015057766 | A1 | 4/2015 |
| WO | 2016110824 | A1 | 7/2016 |
| WO | 2016123278 | A1 | 8/2016 |
| WO | 2016139590 | A1 | 9/2016 |
| WO | 2016139597 | A2 | 9/2016 |
| WO | 2016176065 | A1 | 11/2016 |
| WO | 2018089275 | A1 | 5/2018 |
| WO | 2018089285 | A1 | 5/2018 |
| WO | 2018089385 | A1 | 5/2018 |
| WO | 2018191547 | A1 | 10/2018 |
| WO | 2018213148 | A1 | 11/2018 |
| WO | 2018218236 | A1 | 11/2018 |
| WO | 2019/146026 | A1 | 8/2019 |
| WO | 2019199734 | A1 | 10/2019 |
| WO | 2020069395 | A1 | 4/2020 |
| WO | 2021050302 | A1 | 3/2021 |
| WO | 2021/077103 | A1 | 4/2021 |
| WO | 2021062023 | A1 | 4/2021 |
| WO | 2021081205 | A1 | 4/2021 |
| WO | 2021086793 | A1 | 5/2021 |
| WO | 2023069553 | A2 | 4/2023 |
| WO | 2023081314 | A1 | 5/2023 |
| WO | 2023141112 | A1 | 7/2023 |
| WO | 2023146773 | A3 | 9/2023 |
| WO | 2024123925 | A2 | 6/2024 |
| WO | 2024129815 | A1 | 6/2024 |

OTHER PUBLICATIONS

PCT/US2021/039843 filed Jun. 30, 2021 International Search Report and Written Opinion dated Nov. 11, 2021.
PCT/US2021/044029 filed Jul. 30, 2021 International Search Report and Written Opinion dated Dec. 9, 2021.
U.S. Appl. No. 16/398,020, filed Apr. 29, 2019 Final Office Action dated Jan. 25, 2022.
U.S. Appl. No. 17/077,728, filed Oct. 22, 2020 Non-Final Office Action dated Feb. 9, 2022.

PCT/US2020/048583 filed Aug. 28, 2020 International Search Report and Written Opinion dated Nov. 13, 2020.
PCT/US2020/052536 filed Sep. 24, 2020 International Search Report and Written Opinion dated Dec. 4, 2020.
PCT/US2020/056364 filed Oct. 19, 2020 International Search Report and Written Opinion dated Jan. 19, 2021.
PCT/US2020/056864 filed Oct. 22, 2020 International Search Report and Written Opinion dated Jan. 14, 2021.
PCT/US2020/057202 filed Oct. 23, 2020 International Search Report and Written Opinion dated Jan. 21, 2021.
PCT/US2020/057397 filed Oct. 26, 2020 International Search Report and Written Opinion dated Mar. 10, 2021.
PCT/US2021/014700 filed Jan. 22, 2021 International Search Report and Written Opinion dated Jun. 29, 2021.
U.S. Appl. No. 15/008,628, filed Jan. 28, 2016 Final Office Action dated May 30, 2018.
U.S. Appl. No. 15/008,628, filed Jan. 28, 2016 Non-Final Office Action dated Jan. 25, 2019.
U.S. Appl. No. 15/008,628, filed Jan. 28, 2016 Non-Final Office Action dated Nov. 2, 2017.
U.S. Appl. No. 15/008,628, filed Jan. 28, 2016 Notice of Allowance dated May 15, 2019.
U.S. Appl. No. 16/398,020, filed Apr. 29, 2019 Non-Final Office Action dated May 11, 2021.
PCT/US2021/028018 filed Apr. 19, 2021 International Search Report and Written Opinion dated Sep. 13, 2021.
PCT/US2021/028683 filed Apr. 22, 2021 International Search Report and Written Opinion dated Sep. 16, 2021.
PCT/US2021/029183 filed Apr. 26, 2021 International Search Report and Written Opinion dated Sep. 24, 2021.
PCT/US2021/033443 filed May 20, 2021 International Search Report and Written Opinion dated Sep. 23, 2021.
EP 20862936.0 filed Mar. 28, 2022 Extended European Search Report dated Sep. 19, 2023.
PCT/US2023/010971 filed Jan. 17, 2023 International Search Report and Written Opinion dated Jul. 28, 2023.
U.S. Appl. No. 17/006,553, filed Aug. 28, 2020 Notice of Allowance dated Sep. 11, 2023.
Yamada, T. et al., "Selective Hemi-Portocaval Shunt Based on Portal Vein Pressure for Small-for-Size Graft in Adult Living Donor Liver Transplantation." American Journal of Transplantation, Blackwell Munksgaard, DK, vol. 8, No. 4, Feb. 5, 2008 [Feb. 5, 2008] pp. 847-853.
U.S. Appl. No. 17/006,553, filed Aug. 28, 2020 Final Office Action dated Sep. 28, 2022.
PCT/US2022/047179 filed Oct. 19, 2022 International Preliminary Report on Patentability dated Apr. 23, 2024.
PCT/US2023/083764 filed Dec. 13, 2023 International Search Report and Written Opinion dated Apr. 22, 2024.
U.S. Appl. No. 17/006,553, filed Aug. 28, 2020 Non-Final Office Action dated Mar. 16, 2022.
PCT/US2022/047179 filed Oct. 19, 2022 International Search Report and Written Opinion dated Apr. 18, 2023.
PCT/US2022/048881 filed Nov. 3, 2022 International Search Report and Written Opinion dated Mar. 31, 2023.
PCT/US2023/010972 filed Jan. 17, 2023 International Search Report and Written Opinion dated May 30, 2023.
U.S. Appl. No. 17/006,553, filed Aug. 28, 2020 Non-Final Office Action dated Jun. 26, 2023.
PCT/US2023/082753 filed Dec. 6, 2023 International Search Report and Written Opinion dated Mar. 29, 2024.
U.S. Appl. No. 17/969,626, filed Oct. 19, 2022 Non-Final Office Action dated Sep. 25, 2025.
U.S. Appl. No. 17/980,455, filed Nov. 3, 2022 Restriction Requirement dated Nov. 19, 2025.
U.S. Appl. No. 18/076,169, filed Dec. 6, 2022 Non-Final Office Action dated Aug. 8, 2025.
U.S. Appl. No. 18/076,169, filed Dec. 6, 2022 Notice of Allowance dated Dec. 5, 2025.
U.S. Appl. No. 18/081,480, filed Dec. 14, 2022 Non-Final Office Action dated Sep. 17, 2025.
U.S. Appl. No. 18/098,052, filed Jan. 17, 2023 Restriction Requirement dated Dec. 5, 2025.

(56)         References Cited

OTHER PUBLICATIONS

U.S. Appl. No. 18/098,059, filed Jan. 17, 2023 Restriction Requirement dated Nov. 20, 2025.
U.S. Appl. No. 17/969,626, filed Oct. 19, 2022 Notice of Allowance dated Jan. 27, 2026.
U.S. Appl. No. 18/098,052, filed Jan. 17, 2023 Non-Final Office Action dated Feb. 23, 2026.
U.S. Appl. No. 18/098,059, filed Jan. 17, 2023 Ex Parte Quayle Action dated Mar. 26, 2026.
U.S. Appl. No. 18/524,480, filed Nov. 30, 2023 Non-Final Office Action dated Mar. 25, 2026.

* cited by examiner

SECTION A

SECTION B

SECTION C

SECTION D or E

① Allow melted polymeric material to exude from exit hole 162 while melting

② Thrust and cut

RAPIDLY INSERTABLE CENTRAL CATHETERS AND METHODS THEREOF

PRIORITY

This application claims the benefit of priority to U.S. Provisional Application No. 63/047,118, filed Jul. 1, 2020, which is incorporated by reference in its entirety into this application.

BACKGROUND

A central venous catheter ("CVC") is formed of a material having a relatively low durometer, which contributes to the CVC having a lack of column strength. Due to the lack of column strength, CVCs are commonly introduced into patients and advanced through their vasculatures by way of the Seldinger technique. The Seldinger technique utilizes a number of steps and medical devices (e.g., a needle, a scalpel, a guidewire, an introducer sheath, a dilator, a CVC, etc.). While the Seldinger technique is effective, the number of steps is time consuming, handling the number of medical devices is awkward, and both of the foregoing can lead to patient trauma. In addition, there is a relatively high potential for touch contamination due to the number of medical devices that need to be interchanged during the number of steps of the Seldinger technique. As such, there is a need to reduce the number of steps and medical devices involved in introducing a catheter such as a CVC into a patient and advancing the catheter through a vasculature thereof.

Disclosed herein are rapidly insertable central catheters ("RICCs") including catheter assemblies and methods thereof that address at least the foregoing.

SUMMARY

Disclosed herein is a RICC including, in some embodiments, a first section, a second section, and a tapered junction of a catheter tube. The first section of the catheter tube is formed of a first polymeric material having a first durometer. The first section is in a distal portion of the catheter tube. The second section of the catheter tube is formed of a second polymeric material having a second durometer less than the first durometer. The second section is in the distal portion of the catheter tube proximal of the first section. The junction of the catheter tube is formed of the second polymeric material, a third polymeric material having a third durometer closer to the second durometer than the first durometer, or a combination thereof. The first section of the catheter tube has a proximal portion disposed in a receptacle of the junction and fixedly coupled thereto. An abluminal surface of a distal portion of the junction smoothly transitions onto an abluminal surface of the proximal portion of the first section without an edge that catches on skin when the RICC is inserted into an insertion site of a patient.

In some embodiments, the edge includes solvent-interdiffused polymeric material of the first polymeric material and the polymeric material of the junction.

In some embodiments, the first polymeric material is polytetrafluoroethylene, polypropylene, or polyurethane.

In some embodiments, the second polymeric material is polyvinyl chloride, polyethylene, polyurethane, or silicone.

In some embodiments, the RICC is a triluminal catheter having a primary lumen, a secondary lumen, and a tertiary lumen. The primary lumen has a primary-lumen aperture in a distal end of the first section of the catheter tube. The secondary lumen has a secondary-lumen aperture in a side of the second section of the catheter tube. The tertiary lumen has a tertiary-lumen aperture in the side of the second section proximal of the secondary-lumen aperture.

In some embodiments, the junction includes the third polymeric material radiofrequency ("RF") welded to the second section of the catheter tube. Only the primary lumen extends from the second section, through the junction, and into the first section.

In some embodiments, the RICC has a column strength sufficient to prevent buckling of the catheter tube when inserted into the insertion site and advanced through a vasculature of the patient.

Also disclosed is a method of making a RICC including, in some embodiments, a mandrel-inserting step, a first catheter tube-inserting step, a melting step, a thrusting step, a first removing step, and a second removing step. The mandrel-inserting step includes inserting a stepped mandrel into a primary lumen of a second section of a catheter tube. The mandrel-inserting step forms a mandrel-mounted catheter tube. The first catheter tube-inserting step includes inserting the mandrel-mounted catheter tube into a cavity of an RF-welding die such that a distal end of the mandrel-mounted catheter tube is short of an end of the RF-welding die. The melting step includes melting polymeric material of the mandrel-mounted catheter tube, supplemental polymeric material, or a combination thereof in the RF-welding die by heating the RF-welding die. Melted polymeric material conforms to the cavity of the RF-welding die during the melting step to form a junction welded to the second section of the catheter tube. The melting step forms a soft portion of the catheter tube including the second section of a catheter tube and the junction. The thrusting step incudes thrusting the mandrel and the soft portion of the catheter tube mounted thereon together into the end of the RF-welding die when excess melted polymeric material exudes through an exit hole in the end of the RF-welding die. By action of the thrusting in the thrusting step, the excess melted polymeric material is cut from a distal end of the soft portion of the catheter tube. The first removing step includes removing the mandrel and the soft portion of the catheter tube mounted thereon together from the RF-welding die. The second removing step includes removing the mandrel from both the primary lumen of the second section of the catheter tube and a receptacle of the junction.

In some embodiments, the method further includes a second catheter tube-inserting step and a coupling step. The second catheter tube-inserting step includes inserting a proximal portion of a hard portion of the catheter tube into the receptacle of the junction. The coupling step includes fixedly coupling the hard and soft portions of the catheter tube together such that an abluminal surface of a distal portion of the junction smoothly transitions onto an abluminal surface of the proximal portion of the first section without an edge that catches on skin when the RICC is inserted into an insertion site of a patient.

In some embodiments, the method further includes a solvent-applying step. The solvent-applying step includes applying solvent to the proximal portion of the hard portion of the catheter tube, the receptacle of the junction, or both. The solvent-applying step is performed before the second catheter tube-inserting step.

In some embodiments, the method further includes a first catheter tube-obtaining step or a first catheter tube-extruding step. The first catheter tube-obtaining step or the first catheter tube-extruding respectively include obtaining or extruding a first section of the catheter tube. The first section is commensurate with the hard portion of the catheter tube.

In some embodiments, the first section of the catheter tube is formed of a first polymeric material having a first durometer, the second section of the catheter tube is formed of a second polymeric material having a second durometer less than the first durometer, and the junction of the catheter tube is formed of the second polymeric material, the supplemental polymeric material, or the combination thereof, the supplemental polymeric material being a third polymeric material having a third durometer closer to the second durometer than the first durometer.

In some embodiments, the method further includes a second catheter tube-obtaining step or a second catheter tube-extruding step. The second catheter tube-obtaining step or the second catheter tube-extruding step respectively include obtaining or extruding the second section of the catheter tube. The second section of the catheter tube is multiluminal with one or more additional lumens to the primary lumen.

In some embodiments, the method further includes a polymeric rod-inserting step. The polymeric rod-inserting step includes inserting one or more polymeric rods into the one-or-more additional lumens before the melting step. The one-or-more polymeric rods provide the supplemental polymeric material.

In some embodiments, the method further includes a sacrificial tube-disposing step. The sacrificial tube-disposing step includes disposing a sacrificial polymeric tube over the stepped mandrel before or after forming the mandrel-mounted catheter tube. The sacrificial polymeric tube provides the supplemental polymeric material.

Also disclosed herein is a method of using a RICC assembly including, in some embodiments, an insertion site-creating step, a RICC-inserting step, and a RICC-advancing step. The insertion site-creating step includes creating an insertion site to access a vasculature of a patient with an introducer needle disposed within a primary lumen of the RICC. The RICC-inserting step includes inserting a distal portion of a catheter tube of the RICC into the insertion site past a tapered junction between a first section of the catheter tube and a second section of the catheter tube without an edge between the first section and the junction catching on skin of the patient during the RICC-inserting step. The RICC-advancing step includes advancing the distal portion of the catheter tube through the vasculature of the patient without use of a Seldinger technique.

In some embodiments, the method further includes a needle-withdrawing step of withdrawing the introducer needle from the primary lumen of the RICC after the insertion site-creating step and inserting at least some of the distal portion of the catheter tube into the insertion site.

In some embodiments, the insertion site is at a right subclavian vein or a right internal jugular vein.

In some embodiments, the RICC-advancing step includes advancing the distal portion of the catheter tube through the right subclavian vein or the right internal jugular vein, a right brachiocephalic vein, and into a superior vena cava.

These and other features of the concepts provided herein will become more apparent to those of skill in the art in view of the accompanying drawings and following description, which describe particular embodiments of such concepts in greater detail.

DRAWINGS

DESCRIPTION

Figure 1:
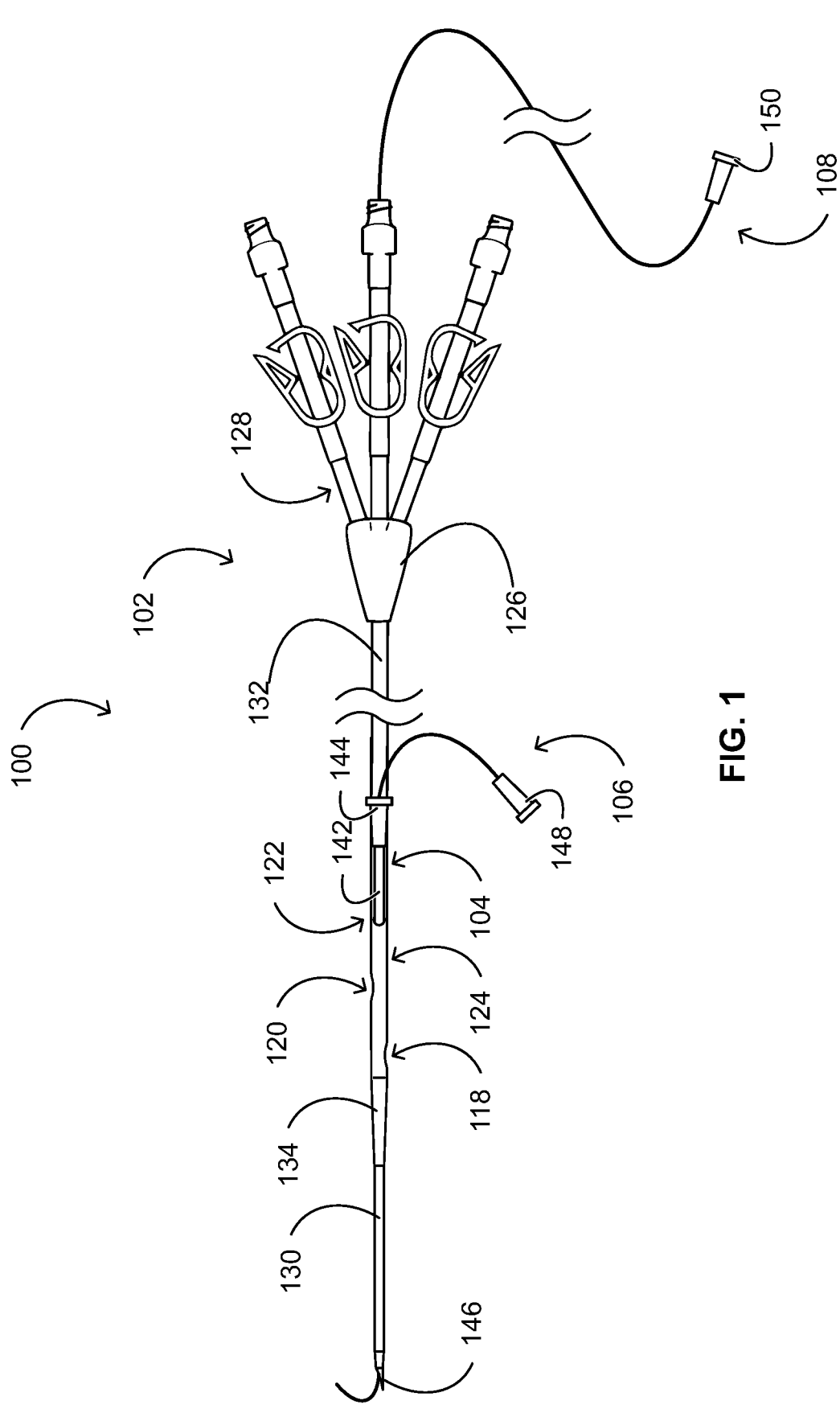
FIG. 1 illustrates a RICC assembly in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

As set forth above, there is a need to reduce the number of steps and medical devices involved in introducing a catheter into a patient and advancing the catheter through a vasculature thereof. Disclosed herein are RICCs and methods thereof that address the foregoing need.

In addition to the need for such RICCs and methods thereof, there is a need to overcome certain artifacts in manufacturing the RICCs. For example, a RICC can be multiluminal but transition to a monoluminal section in a distal portion thereof, which transition is considerably difficult to manufacture without creating an edge or bump that catches skin of a patient around an insertion site and resists insertion of the RICC. Therefore, also disclosed herein are RICCs and methods thereof that address the foregoing need.

Rapidly Insertable Central Catheters

FIG. 1 illustrates a RICC assembly 100 in accordance with some embodiments.

As shown, the RICC assembly 100 includes the RICC 102, an introducer needle 104, an access guidewire 106, and a maneuver guidewire 108 coupled together in a ready-to-deploy state of the RICC assembly 100. Each of the foregoing components of the RICC assembly 100 are described, in turn, in sections set forth below; however, some crossover between the sections for the RICC 102, the introducer needle 104, the access guidewire 106, and the maneuver guidewire 108 exist in view of their interrelatedness in the RICC assembly 100.

The RICC 102 can be a monoluminal or multiluminal RICC (e.g., a diluminal RICC, a triluminal RICC, a tetraluminal RICC, a pentaluminal RICC, a hexaluminal RICC, etc.). Indeed, the RICC 102 shown in FIG. 1 is triluminal including a set of three lumens. Such a set of three lumens includes a primary lumen 110 (e.g., a distal lumen), a secondary lumen 112 (e.g., a medial lumen), and a tertiary lumen 114 (e.g., a proximal lumen) formed of fluidly connected portions of three catheter-tube lumens, three hub lumens, and three extension-leg lumens. (See FIGS. 2 and 3-6.)

Whether the RICC 102 is monoluminal or multiluminal, the RICC 102 includes at least the primary lumen 110. The primary lumen 110 typically extends from a proximal end of the RICC 102 to a distal end of the RICC 102 such as from an opening of a corresponding Luer connector to a primary-lumen aperture 116 in a distal end of the catheter tube 124 (e.g., the hard portion of the catheter tube 124 or the first section of the catheter tube 124) set forth below. When the RICC 102 has two or more lumens, the RICC 102 further includes at least the secondary lumen 112. The secondary lumen 112 typically extends from the proximal end of the RICC 102 to a distal portion of the RICC 102 such as from an opening of a corresponding Luer connector to a secondary-lumen aperture 118 in the distal portion of the catheter tube 124 (e.g., the soft portion of the catheter tube 124 or the second section of the catheter tube 124) proximal of the primary-lumen aperture 116. When the RICC 102 has three or more lumens, the RICC 102 further includes at least the tertiary lumen 114. The tertiary lumen 114 typically extends from the proximal end of the RICC 102 to the distal portion of the RICC 102 such as from an opening of a corresponding Luer connector to a tertiary-lumen aperture 120 in the distal portion of the catheter tube 124 (e.g., the soft portion of the catheter tube 124 or the first section of the catheter tube 124) proximal of the secondary-lumen aperture 118. Notwithstanding the foregoing, each lumen of the secondary lumen 112 and the tertiary lumen 114 can distally extend slightly farther than the secondary-lumen aperture 118 and the tertiary-lumen aperture 120, respectively, in view of different manufacturing methods. (See FIGS. 2, 5, and 6.)

The RICC 102 is shown with an introducing aperture 122, which is dedicated to accommodating insertion of the introducer needle 104 therethrough for coupling the RICC 102 and the introducer needle 104 together in the RICC assembly 100. However, the RICC 102 need not include a dedicated introducing aperture such as the introducing aperture 122. Indeed, the secondary-lumen aperture 118 or the tertiary-lumen aperture 120 can serve as the introducing aperture 122 in some embodiments, which requires a different mode of coupling the RICC 102 and the introducer needle 104 as set forth below. Alternatively, such as when the RICC 102 is monoluminal, an introducing aperture can be created as needed by puncturing the catheter tube 124 with the introducer needle 104.

The RICC 102 further includes an introducing lumen coincident with a distal portion of the primary lumen 110. In other words, the introducing lumen is an introducing portion of the primary lumen 110 of the RICC 102. In the RICC 102, the introducing lumen is the distal portion of the primary lumen 110 extending from the introducing aperture 122 to the primary-lumen aperture 116. The introducing aperture 122, which can be distal of the secondary-lumen aperture 118, between the secondary-lumen aperture 118 and the tertiary-lumen aperture 120, or proximal of the tertiary-lumen aperture 120, opens directly into a proximal end of the introducing portion of the primary lumen 110 of the RICC 102. For a RICC without the introducing aperture 122, the introducing lumen is the distal portion of the primary lumen 110 extending from the secondary-lumen aperture 118, the tertiary-lumen aperture 120, or a puncture created with the introducer needle 104 to the primary-lumen aperture 116. Whether the introducing lumen extends from the secondary-lumen aperture 118, the tertiary-lumen aperture 120, or the puncture depends upon which aperture of the foregoing apertures accommodates the introducer needle 104. Neither the secondary-lumen aperture 118 nor the tertiary-lumen aperture 120 opens directly into a proximal end of the introducing portion of the primary lumen 110 of the RICC without the introducing aperture 122. Instead, the introducer needle 104 pierces a septum 123 between the secondary lumen 112 or the tertiary lumen 114 and the primary lumen 110 respectively by way of the secondary-lumen aperture 118 or the tertiary-lumen aperture 120.

The RICC 102 includes a catheter tube 124, a catheter hub 126, and one or more extension legs 128.

Figure 2:
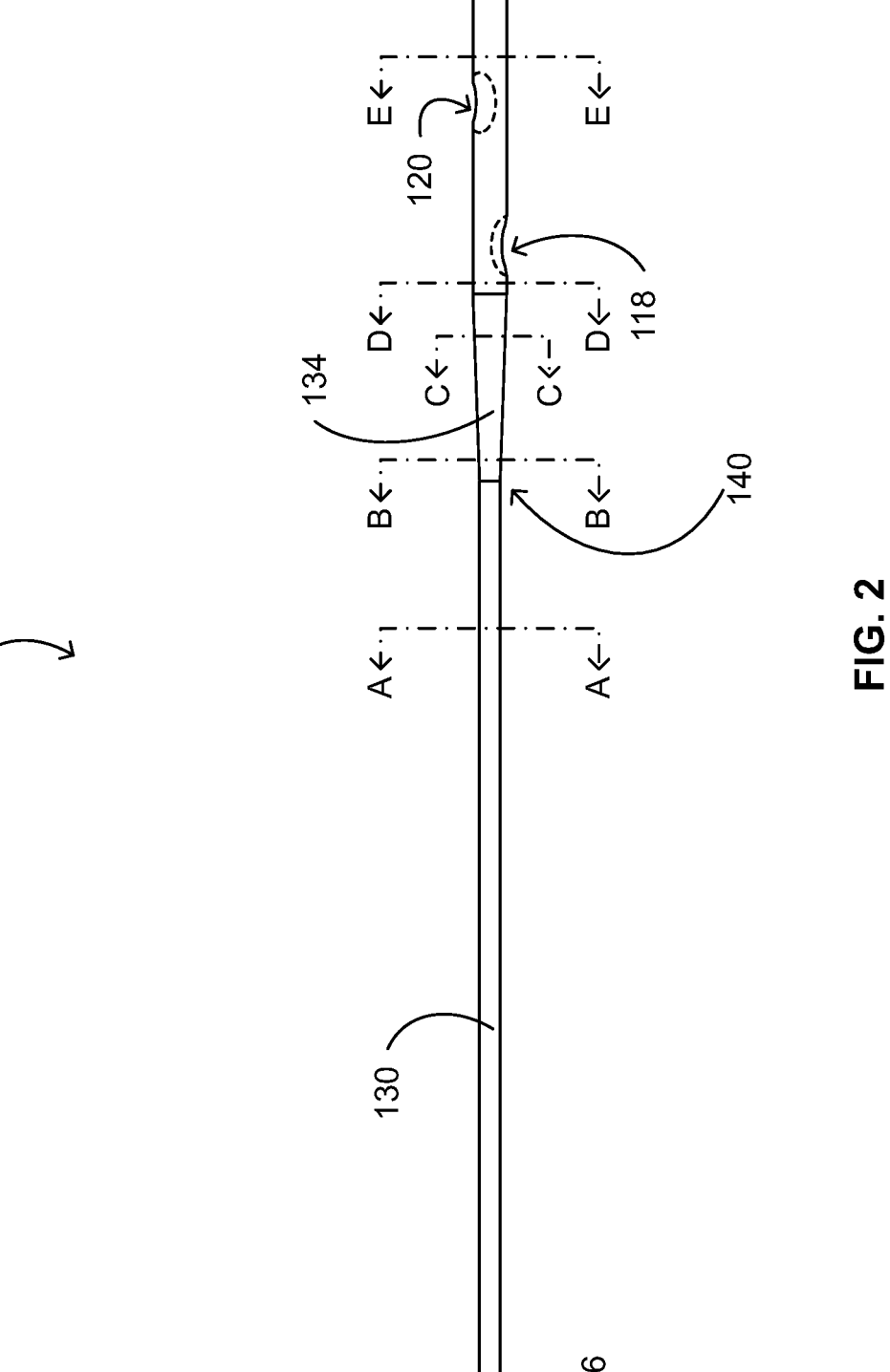
FIG. 2 illustrates a distal portion of a catheter tube of the RICC of FIG. 1 in accordance with some embodiments.
Figure 3:
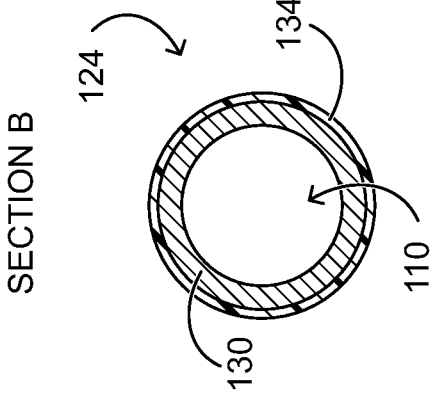
FIG. 3 illustrates a first transverse cross section of the catheter tube of FIG. 2 in accordance with some embodiments.
Figure 4:
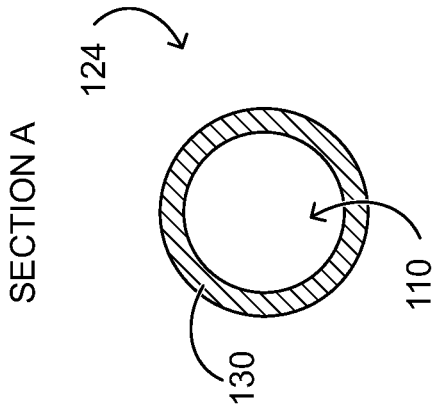
FIG. 4 illustrates a second transverse cross section of the catheter tube of FIG. 2 in accordance with some embodiments.
Figure 5:
FIG. 5 illustrates a third transverse cross section of the catheter tube of FIG. 2 in accordance with some embodiments.
Figure 6:
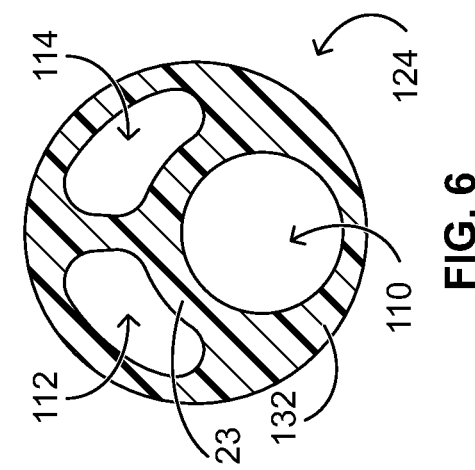
FIG. 6 illustrates a fourth transverse cross section of the catheter tube of FIG. 2 in accordance with some embodiments.

FIG. 2 illustrates a distal portion of the catheter tube 124 of the RICC 102 of FIG. 1 in accordance with some embodiments. FIGS. 3-6 illustrate various transverse cross sections of the catheter tube 124 of FIG. 2 in accordance with some embodiments.

The catheter tube 124 includes a hard portion of the catheter tube 124 and a soft portion of the catheter tube 124, wherein "hard" and "soft" are used in a relative sense in that the hard portion of the catheter tube 124 is harder than the soft portion of the catheter tube 124. Likewise, the soft portion of the catheter tube 124 is softer than the hard portion of the catheter tube 124. The hard potion of the catheter tube 124 includes a first section 130 in a distal portion of the catheter tube 124, and the soft potion of the catheter tube 124 includes a second section 132 extending from a proximal portion of the catheter tube 124 to the distal portion thereof but proximal of the first section 130. Notwithstanding a tapered junction 134 of the catheter tube 124 including a proximal portion of the hard portion of the catheter tube 124 in the RICC 102, the soft portion of the catheter tube 124 is generally considered to include the junction 134 in view of its construction. Together, the foregoing arrangement of the first section 130 of the catheter tube 124, the second section 132 of the catheter tube 124, and the junction 134 possess a column strength sufficient to prevent buckling of the catheter tube 124 when inserted into an insertion site established by a percutaneous puncture and advanced through a vasculature of a patient.

Each of the first section 130, the second section 132, and the junction 134 of the catheter tube 124 is set forth in more detail below.

Like that set forth above for the RICC 102, the catheter tube 124 can be monoluminal or multiluminal. Indeed, the catheter tube 124 includes one or more catheter-tube lumens corresponding in name and number to those of the RICC 102. The one-or-more catheter-tube lumens extend through the catheter tube 124 as set forth above for the RICC 102.

And like that set forth above for the RICC 102, the catheter tube 124 is shown with the introducing aperture 122 through a side of the catheter tube 124 in the distal portion thereof. Again, the introducing aperture 122 is dedicated to accommodating insertion of the introducer needle 104 therethrough for coupling the RICC 102 and the introducer needle 104 together in the RICC assembly 100. However, neither the RICC 102 nor the catheter tube 124 needs to include a dedicated introducing aperture. Indeed, not including the introducing aperture 122, a catheter tube can include n-1 side apertures through a side of the catheter tube in accordance with a number of lumens n of a RICC. Any side aperture of the n-1 side apertures can serve as the introducing aperture 122 in embodiments of a RICC lacking a dedicated introducing aperture. In consideration of a RICC having three lumens like the RICC 102 set forth above, the catheter tube of such a RICC includes two side apertures such as the secondary-lumen aperture 118 and the tertiary-lumen aperture 120 set forth above. In addition to providing different apertures for aspirating blood, delivering fluids, or the like, any side aperture of such side apertures can serve as the introducing aperture 122 for coupling the RICC and the introducer needle 104 together in a corresponding RICC assembly.

The first section 130 of the catheter tube 124 is in the distal portion of the catheter tube 124. The first section 130 includes a distal tip 136 having a relatively short taper continuing from the beveled tip 146 of the introducer needle 104 in the RICC assembly 100 to an outer diameter of a remainder of the first section 130. The taper of the distal tip 136 is configured for immediate dilation of tissue about a percutaneous puncture established with the introducer needle 104 up to the outer diameter of the remainder of the first section 130 of the catheter tube 124. The first section 130 also includes a proximal portion disposed in the receptacle 138 of the junction 134 and fixedly coupled (e.g., solvent bonded, adhered, welded, etc.) thereto.

The first section 130 of the catheter tube 124 is formed of a first polymeric material having a first durometer. The first polymeric material can be polytetrafluoroethylene, polypropylene, or polyurethane, but the first polymeric material is not limited to the foregoing polymers. Polyurethane is advantageous in that the first section 130 of the catheter tube 124 can be relatively rigid at room-temperature but become more flexible in vivo at body temperature, which reduces irritation to vessel walls and phlebitis.

The second section 132 of the catheter tube 124 extends from the proximal portion of the catheter tube 124 to the distal portion thereof but proximal of the first section 130 of the catheter tube 124. The second section 132 includes a distal end integral (e.g., RF welded) with a proximal end of the junction 134 and a proximal portion disposed in the catheter hub 126 and fixedly coupled (e.g., solvent bonded, welded, adhered, etc.) thereto.

The second section 132 of the catheter tube 124 is formed of a second polymeric material having a second durometer less than the first durometer. The second polymeric material can be polyvinyl chloride, polyethylene, polyurethane, or silicone, but the second polymeric material is not limited to the foregoing polymers. In addition to that set forth above for polyurethane in the first section 130 of the catheter tube 124, polyurethane is advantageous in that it can be less thrombogenic than some other polymers.

The junction 134 of the catheter tube 124 couples the first and second sections 130 and 132 of the catheter tube 124 together. The junction 134 includes a receptacle 138 (see FIG. 10) in a distal portion including the proximal portion of the first section 130 of the catheter tube 124 disposed therein and fixedly coupled (e.g., solvent bonded, welded, adhered, etc.) thereto. The proximal end of the junction 134 is integral (e.g., RF welded) with the distal end of the second section 132 of the catheter tube 124, which, effectively terminates lumens of the second section 132 of the catheter tube 124 other than the primary lumen 110 from passing through the junction 134. The junction 134 also includes a taper over its length from a distal end to the proximal end configured for immediate dilation of tissue about the percutaneous puncture up to an outer diameter of the second section 132 of the catheter tube 124. An abluminal surface of the junction 134 smoothly transitions from an abluminal surface of the proximal portion of the first section 130 without an edge 140 that catches on skin when the RICC 102 is inserted into an insertion site of a patient. In addition to the edge 140 being minimal to negligible, the edge 140 can include solvent-interdiffused polymeric material of the first polymeric material and the polymeric material of the junction 134, which smoothens the transition from the first section 130 of the catheter tube 124 to the junction 134.

The junction 134 of the catheter tube 124 is formed of the second polymeric material or a third polymeric material having a third durometer closer to the second durometer than the first durometer. Again, the second polymeric material can be polyvinyl chloride, polyethylene, polyurethane, or silicone, but the second polymeric material is not limited to the foregoing polymers.

Again, the first section 130 of the catheter tube 124 is formed of a first polymeric material having a first durometer, the second section 132 of the catheter tube 124 is formed of a second polymeric material having a second durometer less than the first durometer, and the junction 134 of the catheter tube 124 is formed of the second polymeric material or a third polymeric material having a third durometer closer to the second durometer than the first durometer. Being that each durometer of the second durometer and the third durometer is less than the first durometer, the soft portion of the catheter tube 124 including the second portion of the catheter tube 124 and the junction 134 is softer than the hard portion of the catheter tube 124 including the first portion of the catheter tube 124. In other words, the first durometer is greater than each durometer of the second durometer and the third durometer. Being that the first durometer is greater than each durometer of the second durometer and the third durometer, the hard portion of the catheter tube 124 including the first portion of the catheter tube 124 is harder than the soft portion of the catheter tube 124 including the second portion of the catheter tube 124 and the junction 134.

It should be understood the first durometer of the first polymeric material, the second durometer of the second polymeric material, and the third durometer of the third polymeric material can be on different scales (e.g., Type A or Type D), so the second durometer or the third durometer might not be numerically less than the first durometer. In other words, the first durometer material might not be numerically greater than the second durometer or the third durometer in view of the different scales. That said, the hardness of the second or third polymeric material can still be less than the hardness of the first polymeric material or the hardness of the first polymeric material can still be greater than the hardness of the second or third polymeric material because the different scales—each of which ranges from 0 to 100—are designed for characterizing different materials in groups of the materials having a like hardness.

Notwithstanding the foregoing, the first section 130 of the catheter tube 124, the second section 132 of the catheter tube 124, and the junction 134 can be formed of a same polymeric material or different polymeric materials having substantially equal durometers provided the column strength of the catheter tube 124 is sufficient to prevent buckling of the catheter tube 124 when inserted into an insertion site established by a percutaneous puncture and advanced through a vasculature of a patient.

The catheter hub 126 is coupled to the proximal portion of the catheter tube 124. The catheter hub 126 includes one or more catheter-hub lumens corresponding in number to the one-or-more catheter-tube lumens. The one-or-more catheter-hub lumens extend through an entirety of the catheter hub 126 from a proximal end of the catheter hub 126 to a distal end of the catheter hub 126.

Each extension leg of the one-or-more extension legs 128 is coupled to the catheter hub 126 by a distal portion of the extension leg. The one-or-more extension legs 128 respectively include one or more extension-leg lumens, which, in turn, correspond in number to the one-or-more catheter-tube lumens. Each extension-leg lumen of the one-or-more extension-leg lumens extends through an entirety of the extension leg from a proximal end of the extension leg to a distal end of the extension leg.

Each extension leg of the one-or-more extension legs 128 typically includes a Luer connector coupled to the extension leg, through which Luer connector the extension leg and the extension-leg lumen thereof can be connected to another medical device.

The introducer needle 104 includes a shaft 142, a needle hub 144 about a proximal portion of the shaft 142, and a beveled tip 146 in a distal portion of the shaft 142.

When the RICC assembly 100 is in the ready-to-deploy state, the introducer needle 104 or the shaft 142 thereof is disposed in the introducing lumen through the introducing aperture 122 (if present), either the secondary-lumen aperture 118 or tertiary-lumen aperture 120 (if the introducing aperture 122 is not present), or a puncture created with the introducer needle 104 such that the beveled tip 146 of the introducer needle 104 extends past the distal end of the first section 130 of the catheter tube 124 for establishing a percutaneous puncture. When the introducer needle 104 or the shaft 142 thereof is disposed in the introducing lumen by way of the secondary-lumen aperture 118 or tertiary-lumen aperture 120, the introducer needle 104 or the shaft 142 thereof is also disposed through the septum 123 dividing the secondary lumen 112 or tertiary lumen 114 from the primary lumen 110.

The access guidewire 106 includes a length sufficient for advancing the access guidewire 106 a sufficient distance into a blood-vessel lumen upon establishing access thereto for advancing the distal portion of the RICC 102 into the blood-vessel lumen for maintaining access.

The access guidewire 106 is disposed in a needle lumen of the introducer needle 104 when the RICC assembly 100 is in at least the ready-to-deploy state. Indeed, a distal end of the access guidewire 106 is proximal of the beveled tip 146 of the introducer needle 104 but distal of the junction 134, which allows for immediate advancement of the distal end of the access guidewire 106 beyond the beveled tip 146 of introducer needle 104 and into a blood-vessel lumen upon establishing access thereto.

The access guidewire 106 includes a stop 148 (e.g., a hub, a ball, a slug, etc.) about a proximal portion of the access guidewire 106 forming a stop end (e.g., a hub end, a ball end, a slug end, etc.) of the access guidewire 106. The stop end of the access guidewire 106 is larger than any aperture of the RICC 102 or the catheter tube 124 thereof, thereby providing a distal limit for advancing the access guidewire 106 into the RICC 102.

The maneuver guidewire 108 includes an atraumatic tip (e.g., a coiled or partially coiled tip) and a length sufficient for advancing the maneuver guidewire 108 to the lower ⅓ of the superior vena cava ("SVC") of the heart.

When the RICC assembly 100 is in at least the ready-to-deploy state, the maneuver guidewire 108 is disposed in the primary lumen 110 of the RICC 102 such that a distal end of the maneuver guidewire 108 is proximal of the introducing aperture 122 but distal of the catheter hub 126, which allows for immediate advancement of the distal end of the maneuver guidewire 108 into the blood-vessel lumen upon removing the introducer needle 104 or the shaft 142 thereof from the introducing lumen. Indeed, the maneuver guidewire 108 cannot be distally advanced into the introducing lumen due the presence of the introducer needle 104 or the shaft 142 thereof in at least the ready-to-deploy state of the RICC assembly 100.

The maneuver guidewire 108 includes a stop 150 (e.g., a hub, a ball, a slug, etc.) about a proximal portion of the maneuver guidewire 108 forming a stop end (e.g., a hub end, a ball end, a slug end, etc.) of the maneuver guidewire 108. The stop end of the maneuver guidewire 108 is larger than a proximal-end opening in the Luer connector of the extension leg in which the maneuver guidewire 108 is disposed, thereby providing a distal limit for advancing the maneuver guidewire 108 into the RICC 102.

Methods

Methods of the RICC assembly 100 include methods of making the RICC assembly 100 and methods of using the RICC assembly 100. FIGS. 7A-7C, 9, and 10 illustrate various steps of a first method of making the RICC 102 of the RICC assembly 100 in accordance with some embodiments. FIGS. 8A-8C, 9, and 10 illustrate various steps of a second method of making the RICC 102 of the RICC assembly 100 in accordance with some embodiments. A method of using the RICC assembly 100 is described after the first and second methods of making the RICC 102 are described.

The first and second methods of making the RICC 102 are alike in that each method includes a mandrel-inserting step, a first catheter tube-inserting step, a melting step, a thrusting step, a first removing step, and a second removing step. The first and second methods primarily differ with respect to adding supplemental polymeric material for the junction 134. Indeed, the first method includes adding the supplemental polymeric material as one or more polymeric rods 152, whereas the second method includes adding the supplemental polymeric material as a sacrificial polymeric tube 154. That said, the methods of making the RICC 102 need not include adding the supplemental polymeric material in accordance with the first method or the second method, for at least an excess distal portion of the second section 132 of the catheter tube 124 can serve as the supplemental polymeric material when making the RICC assembly 100. The excess distal portion of the second section 132 when making the RICC assembly 100 is that in excess of what is needed for the second section 132 of the catheter tube 124 in the RICC 102. It is that which forms the junction 134. Steps for adding the supplemental polymeric material in accordance with the first and second methods are initially described followed by steps common to the first and second methods, which are described, in turn, in sections set forth below.

Notwithstanding the foregoing, whether the first method or the second method of making the RICC 102 is practiced, each method of the first and second methods includes a second catheter tube-obtaining step or a second catheter tube-forming step, which is named so as to correspond to the second section 132 of the catheter tube 124. The second catheter tube-obtaining step or the second catheter tube-forming step respectively includes obtaining or forming the second section 132 of the catheter tube 124 of the second polymeric material having the second durometer. The second catheter tube-forming step includes forming the second section 132 of the catheter tube 124, for example, by extruding the second section 132, cutting the second section 132 to an appropriate length, or the like. The second section 132 of the catheter tube 124 can be monoluminal or multiluminal with one or more additional lumens to the primary lumen 110.

Figure 7A:
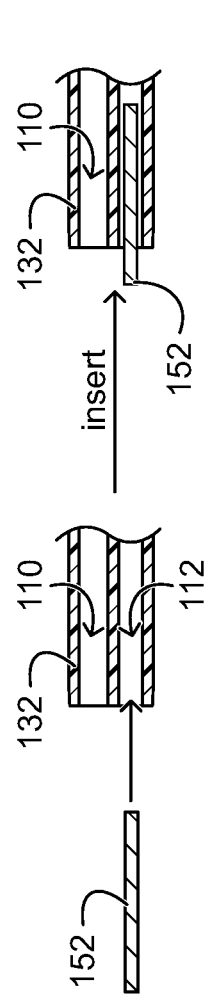
FIG. 7A illustrates a polymeric rod-inserting step of a first method of making the RICC of FIG. 1 in accordance with some embodiments.

As shown in FIG. 7A, the first method of making the RICC 102 includes a polymeric rod-inserting step. The polymeric rod-inserting step includes inserting the one-or-more polymeric rods 152 (e.g., ≤~½″ of each polymeric rod of the one-or-more polymeric rods 152) into the one-or-more additional lumens of the second section 132 of the catheter tube 124. The one-or-more polymeric rods 152 provide the supplemental polymeric material for the junction 134, which can be the second polymeric material or the third polymeric material set forth above. The one-or-more additional lumens are those in addition to the primary lumen 110 in multiluminal RICCs. Such one-or-more additional lumens include, for example, the secondary lumen 112 or the tertiary lumen 114. The polymeric rod-inserting step can be before or after the mandrel-inserting step, but it is most easily performed before the mandrel-inserting step on account of the smaller diameter of each lumen of the one-or-more additional lumens compared to the larger diameter of the primary lumen 110. Indeed, it can be more difficult finding the one-or-more additional lumens when a stepped mandrel 156 is already disposed in the primary lumen 110 and potentially blocking the one-or-more additional lumens.

Figure 8A:
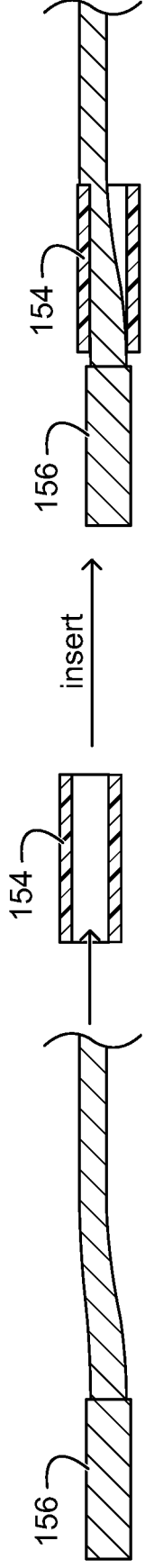
FIG. 8A illustrates a sacrificial tube-disposing step of a second method of making the RICC of FIG. 1 in accordance with some embodiments.

As shown in FIG. 8A, the second method of making the RICC 102 includes a sacrificial tube-disposing step. The sacrificial tube-disposing step includes disposing the sacrificial polymeric tube 154 (e.g., ~½″ of the sacrificial polymeric tube 154) over the mandrel 156. The sacrificial polymeric tube 154 provides the supplemental polymeric material for the junction 134, which can be the second polymeric material or the third polymeric material set forth above. The sacrificial tube-disposing step can be before or after the mandrel-inserting step, but it is most easily performed before the mandrel-inserting step on account of the smaller diameter of a main body of the mandrel 156 compared to the larger diameter of the stepped portion of the mandrel 156. Indeed, it can be more difficult directly disposing the sacrificial polymeric tube 154 over the larger diameter of the stepped portion of the mandrel 156 than the smaller diameter of the main body of the mandrel 156 in view of the tighter tolerances between the sacrificial polymeric tube 154 and the stepped portion of the mandrel 156. While the sacrificial polymeric tube 154 is shown over the main body of the mandrel 156, it should be understood the sacrificial polymeric tube 154 can be disposed over the stepped portion of the mandrel 156. It just might be more difficult to directly do so in accordance with the foregoing.

Advantageously, the second method of making the RICC 102 is useful for monoluminal RICCs, which do not include the one-or-more additional lumens to the primary lumen 110. Indeed, if the first method of making the RICC 102 and the polymeric rod-inserting step thereof was used for a monoluminal RICC, the one-or-more polymeric rods 152 would block the one and only primary lumen 110 with the supplemental polymeric material in the RICC 102.

Whether the first method or the second method of making the RICC 102 is practiced, each method of the first and second methods includes the mandrel-inserting step, the first catheter tube-inserting step, the melting step, the thrusting step, the first removing step, and the second removing step set forth above.

Figure 7B:
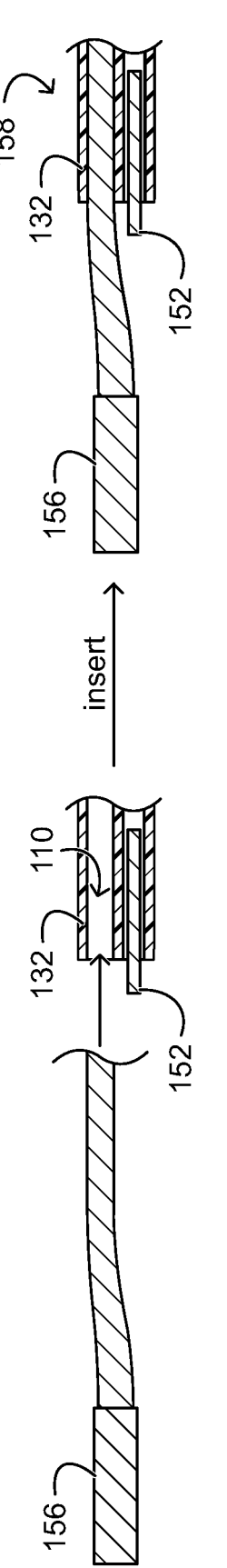
FIG. 7B illustrates a mandrel-inserting step of the first method of making the RICC of FIG. 1 in accordance with some embodiments.
Figure 8B:
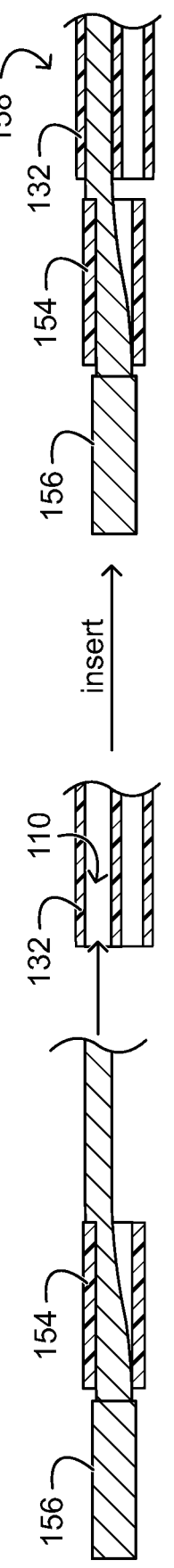
FIG. 8B illustrates a mandrel-inserting step of the second method of making the RICC of FIG. 1 in accordance with some embodiments. a mandrel-inserting step

As shown in FIGS. 7B and 8B, the mandrel-inserting step includes inserting the mandrel 156 into the primary lumen 110 of the second section 132 of the catheter tube 124 to form a mandrel-mounted catheter tube 158. While the stepped portion of the mandrel 156 is shown some distance away from a distal end of the second section 132 of the catheter tube 124, it should be understood the stepped portion of the mandrel 156 can abut the distal end of the second section 132. Indeed, inserting the mandrel 156 into the primary lumen 110 of the second section 132 of the catheter tube 124 such that the stepped portion of the mandrel 156 is as close as possible to the distal end of the second section 132 is preferred. As shown in FIG. 7B, the mandrel-mounted catheter tube 158 further includes the one-or-more polymeric rods 152 disposed in the one-or-more additional lumens. As shown in FIG. 8B, the mandrel-mounted catheter tube 158 further includes the sacrificial polymeric tube 154 disposed over the mandrel 156.

Figures 7C, 9:
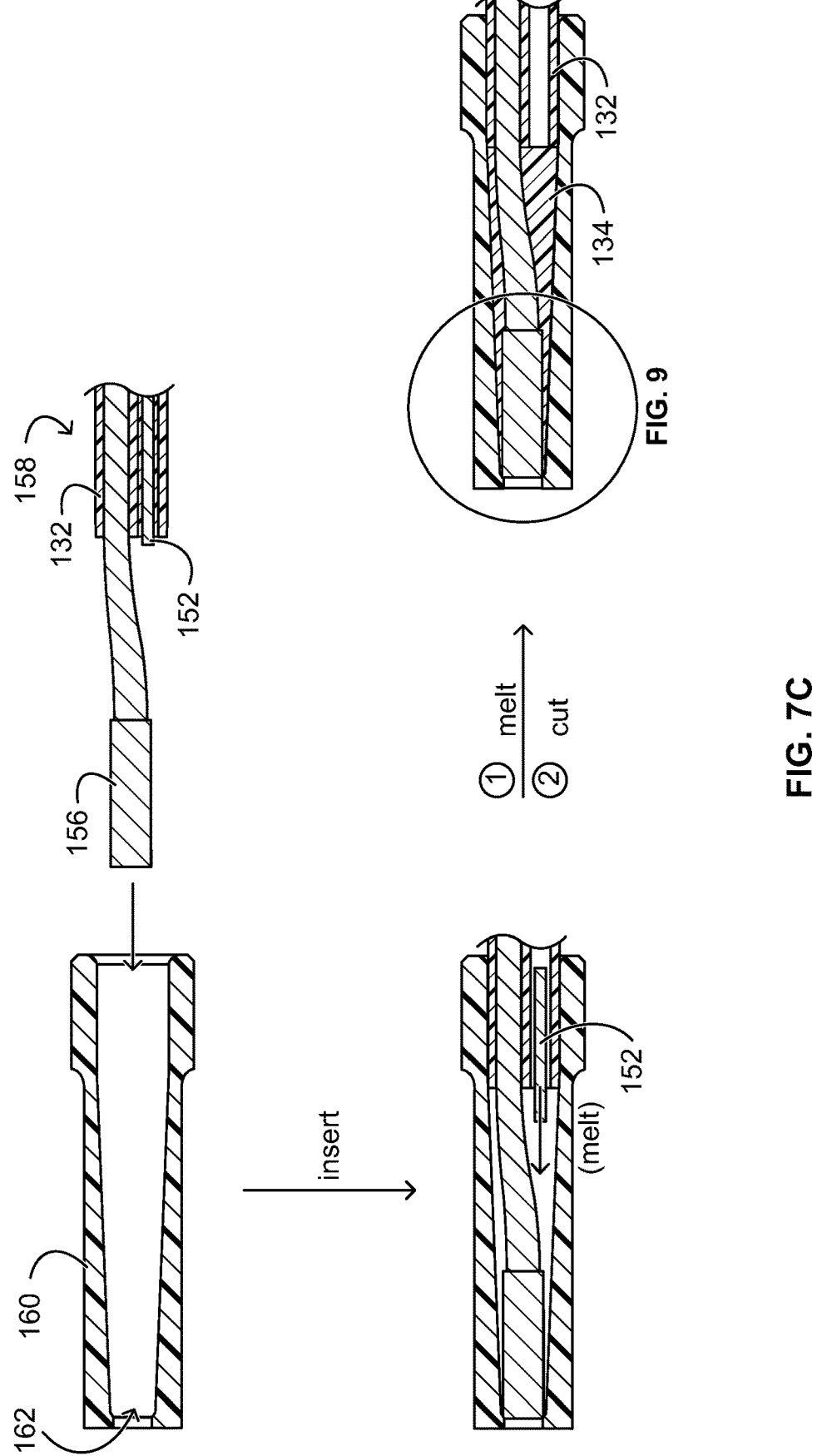
FIG. 7C illustrates a melting step and a thrusting step of the first method of making the RICC of FIG. 1 in accordance with some embodiments.
FIG. 9 illustrates a detailed view of the melting step and the thrusting step of either the first method or second method of making the RICC of FIG. 1 in accordance with some embodiments.
Figures 8C, 9:
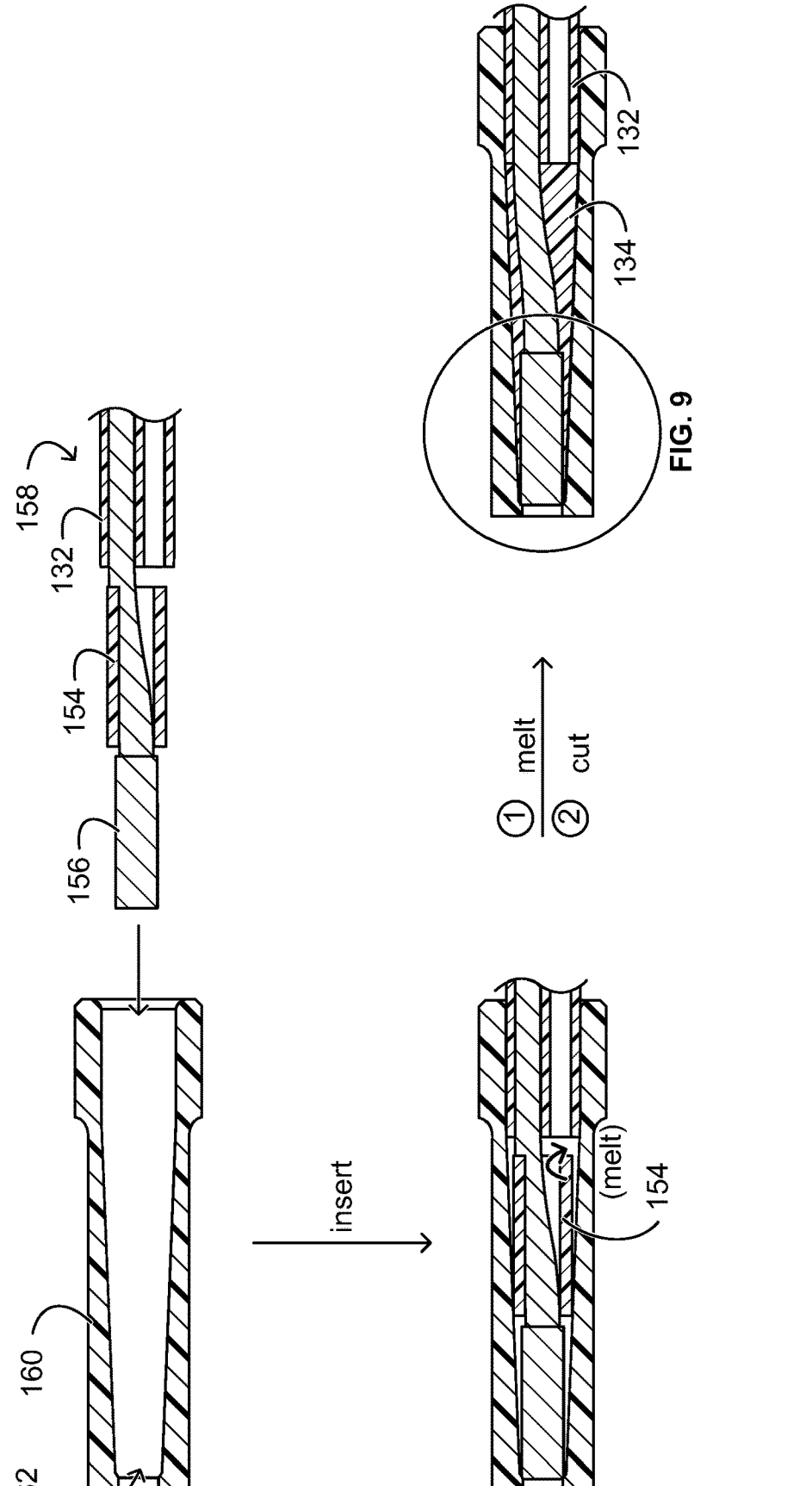
FIG. 8C illustrates a melting step and a thrusting step of the second method of making the RICC of FIG. 1 in accordance with some embodiments.
Figure 9:
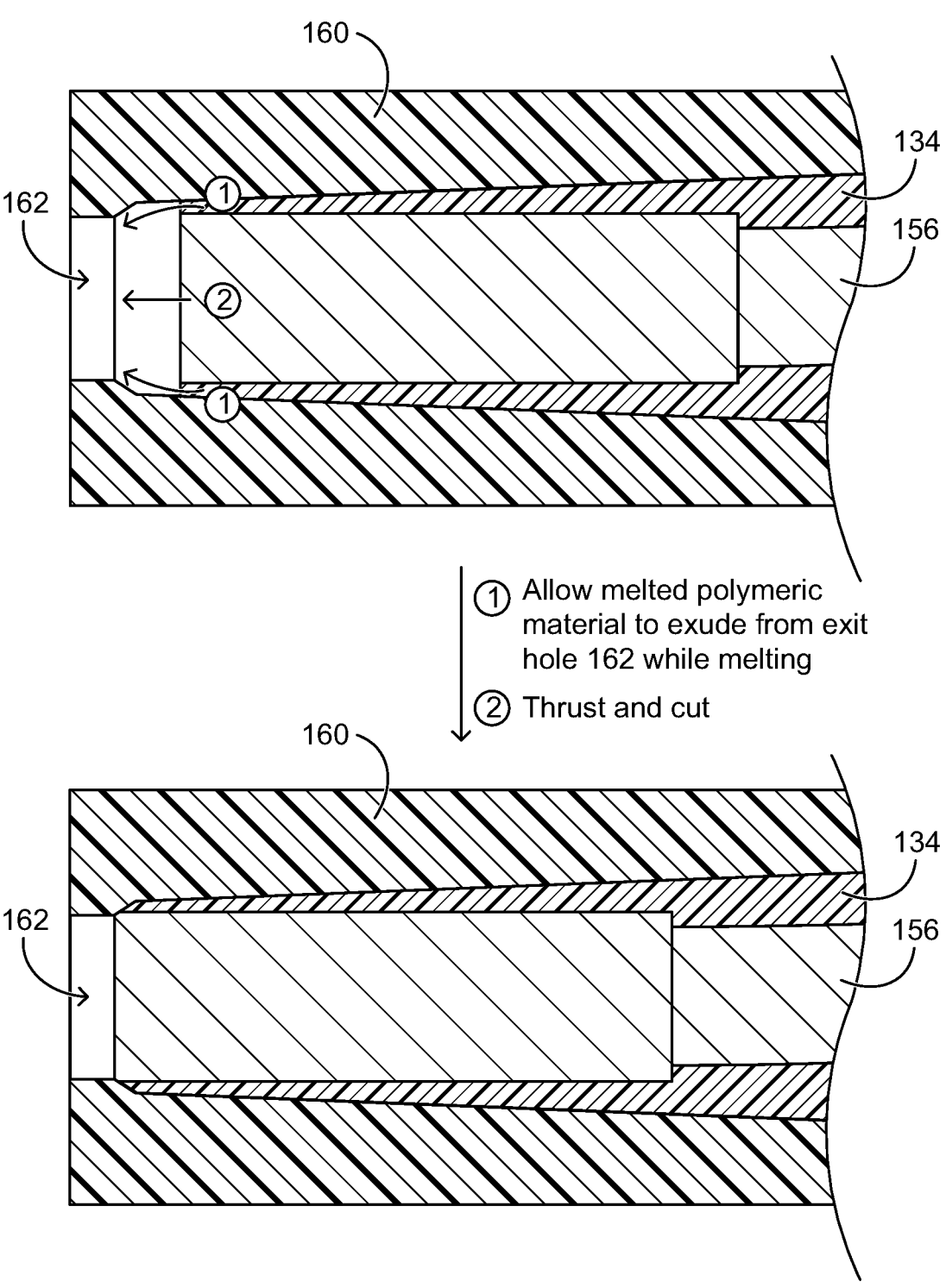

As shown in FIGS. 7C and 8C, the first catheter tube-inserting step includes inserting the mandrel-mounted catheter tube 158 into a cavity of an RF-welding die 160 such that a distal end of the mandrel-mounted catheter tube 158 is short of an end of the RF-welding die 160.

As further shown in FIGS. 7C and 8C, as well as FIG. 9, the melting step includes melting polymeric material of the mandrel-mounted catheter tube 158, supplemental polymeric material, or a combination thereof in the RF-welding die 160 by heating the RF-welding die 160. Melted polymeric material conforms to the cavity of the RF-welding die 160 during the melting step to form the junction 134 welded to the second section 132 of the catheter tube 124. The melting step forms the soft portion of the catheter tube 124 including the second section 132 of the catheter tube 124 and the junction 134.

As shown in FIG. 9, the thrusting step incudes thrusting the mandrel 156 and the soft portion of the catheter tube mounted thereon together into the end of the RF-welding die 160 when excess melted polymeric material exudes through an exit hole 162 in the end of the RF-welding die 160. By action of the thrusting in the thrusting step, the excess melted polymeric material is cut from a distal end of the soft portion of the catheter tube 124.

The first removing step includes removing the mandrel 156 and the soft portion of the catheter tube 124 mounted thereon together from the RF-welding die 160.

The second removing step includes removing the mandrel 156 from both the primary lumen 110 of the second section 132 of the catheter tube 124 and the receptacle 138 of the junction 134.

Whether the first method or the second method of making the RICC 102 is practiced, each method of the first and second methods includes a first catheter tube-obtaining step or a first catheter tube-extruding step, which is named so as to correspond to the first section 130 of the catheter tube 124. The first catheter tube-obtaining step or the first catheter tube-forming step respectively includes obtaining or forming the first section 130 of the catheter tube 124 of the first polymeric material having the first durometer. The first catheter tube-forming step includes forming the first section 130 of the catheter tube 124, for example, by extruding the first section 130, cutting the first section 130 to an appropriate length, or the like. The first section 130 is commensurate with the hard portion of the catheter tube 124.

Whether the first method or the second method of making the RICC 102 is practiced, each method of the first and second methods can further include an applying step, a second catheter tube-inserting step, a coupling step, and an aperture-creating step.

The applying step includes a solvent-applying step of applying solvent or an adhesive-applying step of applying an adhesive to the proximal portion of the hard portion of the catheter tube 124, the receptacle 138 of the junction 134 of the soft portion of the catheter tube 124, or both. The applying step is performed before the second catheter tube-inserting step.

Figure 10:
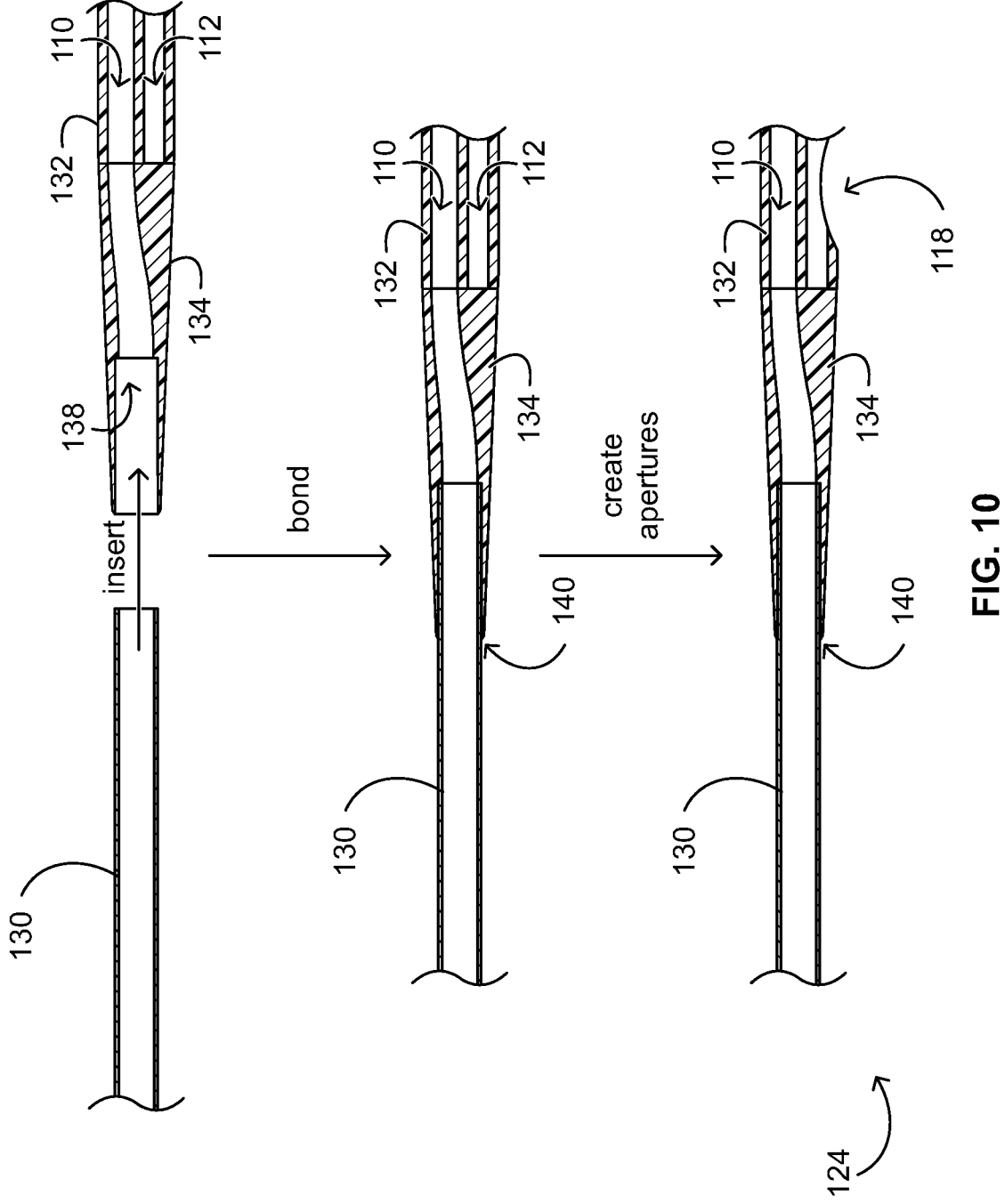
FIG. 10 illustrates a second catheter tube-inserting step and a coupling step of the method in accordance with some embodiments.

As shown in FIG. 10, the second catheter tube-inserting step includes inserting the proximal portion of the hard portion of the catheter tube 124 (i.e., the first section 130 of the catheter tube 124) into the receptacle 138 of the junction 134. Notably, an inner diameter of the first section 130 of the catheter tube 124 and an inner diameter of the portion of the primary lumen 110 in the junction 134 match subsequent to the second catheter tube-inserting step. This eliminates difficulties with guidewires catching between luminal surfaces of the first section 130 of the catheter tube and the junction 134.

The coupling step includes allowing the solvent to evaporate after the second catheter tube-inserting step, thereby forming a solvent-bonded junction between the first section 130 of the catheter tube 124 and the junction 134 with solvent-interdiffused polymeric material of the first polymeric material and the polymeric material of the junction 134. If adhesive is used, the coupling step includes allowing the adhesive to dry (i.e., evaporate its solvent) after the inserting step, thereby forming an adhesive-bonded junction between the first section 130 of the catheter tube 124 and the junction 134 optionally also with solvent-interdiffused polymeric material of the first polymeric material, the polymeric material of the junction 134, and the adhesive. Thus, the coupling step fixedly couples the hard and soft portions of the catheter tube 124 together such that an abluminal surface of a distal portion of the junction 134 smoothly transitions onto an abluminal surface of the proximal portion of the first section 130 over the edge 140 without catching on skin when the RICC 102 is inserted into an insertion site of a patient.

As shown in FIG. 10, the aperture-creating step includes creating one or more apertures such as the secondary-lumen aperture 118 or the tertiary-lumen aperture 120 in the distal portion of the catheter tube 124 for each additional lumen of the one-or-more additional lumens. The aperture-creating step can include an aperture-puncturing step of puncturing the catheter tube 124 to form the one-or-more apertures or an aperture-melting step of melting the catheter tube 124 to form the one-or-more apertures.

In view of the foregoing methods of making the RICC 102, the first section 130 of the catheter tube 124 is formed of the first polymeric material having the first durometer, the second section 132 of the catheter tube 124 is formed of the second polymeric material having the second durometer less than the first durometer, and the junction 134 of the catheter tube 124 is formed of the second polymeric material, the supplemental polymeric material, or the combination thereof, the supplemental polymeric material being the third polymeric material having the third durometer closer to the second durometer than the first durometer.

The method of using the RICC assembly 100 or the RICC 102 thereof includes an insertion site-creating step, a RICC-inserting step, and a RICC-advancing step.

The insertion site-creating step includes creating an insertion site to access a vasculature of a patient with the introducer needle 104 disposed within the primary lumen 110 of the RICC 102. The insertion site can be at a subclavian vein such as a right or left subclavian vein, an internal jugular vein such as a right or left internal jugular vein, or a femoral vein.

The RICC-inserting step includes inserting a distal portion of the catheter tube 124 of the RICC 102 into the insertion site up to past the junction 134 between the first section 130 of the catheter tube 124 and the second section 132 of the catheter tube 124 without the edge 140 between the first section 130 and the junction 134 catching on skin of the patient during the RICC-inserting step. Optionally, the RICC-inserting step is prefaced by an access guidewire-inserting step and the following needle-withdrawing step. The access guidewire-inserting step includes inserting the access guidewire 106 through the distal end of the introducer needle 104 and into one of the foregoing veins.

The method further includes a needle-withdrawing step. The needle-withdrawing step includes withdrawing the introducer needle 104 from the primary lumen 110 of the RICC 102 after the insertion site-creating step and inserting at least some of the distal portion of the catheter tube 124 into the insertion site.

The RICC-advancing step includes advancing the distal portion of the catheter tube 124 through the vasculature of the patient without use of a Seldinger technique. For example, if the insertion site is at the right subclavian vein or the right internal jugular vein, the RICC-advancing step can include advancing the distal portion of the catheter tube 124 through the right subclavian vein or the right internal jugular vein, a right brachiocephalic vein, and into a superior vena cava. Other insertions sites such as at the left subclavian vein or the left internal jugular vein require advancing the distal portion of the catheter tube 124 through corresponding vasculature. Optionally, the RICC-advancing step is prefaced by a maneuver guidewire-inserting step of inserting the maneuver guidewire 108 through the distal end of the RICC 102 and to a target location (e.g., superior vena cava).

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A rapidly insertable central catheter ("RICC"), comprising:
   a first section of a catheter tube formed of a first polymeric material having a first durometer, the first section in a distal portion of the catheter tube;
   a second section of the catheter tube formed of a second polymeric material having a second durometer less than the first durometer, the second section in the distal portion of the catheter tube proximal of the first section; and
   a tapered junction of the catheter tube formed of the second polymeric material, a third polymeric material having a third durometer closer to the second durometer than the first durometer, or a combination thereof, the first section of the catheter tube having a proximal portion disposed in a receptacle of the tapered junction and fixedly coupled thereto such that an abluminal surface of a distal portion of the tapered junction smoothly transitions onto an abluminal surface of the proximal portion of the first section with a minimal to negligible edge configured to not catch on skin when the RICC is inserted into an insertion site of a patient, wherein the minimal to negligible edge includes solvent-interdiffused polymeric material of the first polymeric material and the second polymeric material of the tapered junction as a result of fixedly coupling the proximal portion of the first section of the catheter tube to the receptacle of the tapered junction by solvent bonding.

2. The RICC of claim 1, wherein the first polymeric material is polytetrafluoroethylene, polypropylene, or polyurethane.

3. The RICC of claim 1, wherein the second polymeric material is polyvinyl chloride, polyethylene, polyurethane, or silicone.

4. The RICC of claim 1, wherein the RICC is a triluminal catheter having a primary lumen with a primary-lumen aperture in a distal end of the first section of the catheter tube, a secondary lumen with a secondary-lumen aperture in a side of the second section of the catheter tube, and a tertiary lumen with a tertiary-lumen aperture in the side of the second section proximal of the secondary-lumen aperture.

5. The RICC of claim 4, wherein the tapered junction includes the third polymeric material, radiofrequency ("RF") welded to the second section of the catheter tube, only the primary lumen extending from the second section, through the tapered junction, and into the first section.

6. The RICC of claim 1, wherein the RICC has a column strength sufficient to prevent buckling of the catheter tube when inserted into the insertion site and advanced through a vasculature of the patient.

7. A rapidly insertable central catheter ("RICC"), comprising:
   a first section of a catheter tube formed of a first polymeric material having a first durometer, the first section in a distal portion of the catheter tube;
   a second section of the catheter tube formed of a second polymeric material having a second durometer less than the first durometer, the second section in the distal portion of the catheter tube proximal of the first section; and
   a tapered junction of the catheter tube formed of a third polymeric material, the first section of the catheter tube having a proximal portion disposed in a receptacle of the tapered junction and bonded thereto such that an abluminal surface of a distal portion of the tapered junction smoothly transitions onto an abluminal surface of the proximal portion of the first section with a minimal to negligible edge that does not catch on skin when the RICC is inserted into an insertion site of a patient, wherein the minimal to negligible edge includes solvent-interdiffused polymeric material of the first polymeric material and the third polymeric material as a result of the proximal portion of the first section of the catheter tube having been bonded to the receptacle of the tapered junction by solvent bonding.

8. The RICC of claim 7, wherein the first polymeric material is polytetrafluoroethylene, polypropylene, or polyurethane, the second polymeric material is polyvinyl chloride, polyethylene, polyurethane, or silicone, and the RICC has a column strength sufficient to prevent buckling of the catheter tube when inserted into the insertion site and advanced through a vasculature of the patient.

9. The RICC of claim 7, wherein the RICC is a triluminal catheter having a primary lumen with a primary-lumen aperture in a distal end of the first section of the catheter tube, a secondary lumen with a secondary-lumen aperture in a side of the second section of the catheter tube, and a tertiary lumen with a tertiary-lumen aperture in the side of the second section proximal of the secondary-lumen aperture.

10. The RICC of claim 9, wherein the junction includes the third polymeric material, radiofrequency ("RF") welded to the second section of the catheter tube, only the primary lumen extending from the second section, through the tapered junction, and into the first section.

\* \* \* \* \*